(12) United States Patent
Bub et al.

(10) Patent No.: US 7,939,597 B2
(45) Date of Patent: May 10, 2011

(54) ACRYLIC ACID AND WATER-ABSORBING POLYMER STRUCTURES BASED ON RENEWABLE RAW MATERIALS AND PROCESS FOR THEIR PRODUCTION BY DEHYDRATION

(75) Inventors: Günther Bub, Marl (DE); Jürgen Mosler, Marl (DE); Franz-Felix Kuppinger, Marl (DE); Andreas Sabbagh, Bensheim (DE); Guido Stochniol, Haltern am See (DE); Jörg Sauer, Dülmen (DE); Markus Winterberg, Datteln (DE); Udo Knippenberg, Marl (DE); Günter Latoschinski, Marl (DE); Franck Furno, Düsseldorf (DE); Thorsten Schwärtzke, Marl (DE); Jörg Leistner, Rheda-Wiedenbrück (DE)

(73) Assignee: Evonik Stockhausen GmbH, Kredfeld (DE)

( * ) Notice: Subject to any disclaimer, the term of this patent is extended or adjusted under 35 U.S.C. 154(b) by 0 days.

(21) Appl. No.: 12/438,256

(22) PCT Filed: Aug. 22, 2007

(86) PCT No.: PCT/EP2007/058745
§ 371 (c)(1),
(2), (4) Date: May 13, 2009

(87) PCT Pub. No.: WO2008/023040
PCT Pub. Date: Feb. 28, 2008

(65) Prior Publication Data
US 2009/0239995 A1    Sep. 24, 2009

(30) Foreign Application Priority Data

Aug. 22, 2006   (DE) .......................... 10 2006 039 205

(51) Int. Cl.
*C08L 33/02* (2006.01)
*C07C 51/16* (2006.01)
*C08F 20/06* (2006.01)
*B01J 8/04* (2006.01)

(52) U.S. Cl. ..................... 524/556; 562/532; 526/317.1; 422/189; 422/134

(58) Field of Classification Search .................. 524/556; 562/532; 526/317.1; 422/189, 134
See application file for complete search history.

(56) References Cited

U.S. PATENT DOCUMENTS

| | | | |
|---|---|---|---|
| 4,259,211 A | 3/1981 | Krabetz et al. | |
| 5,264,625 A | 11/1993 | Hammon et al. | |
| 5,387,720 A | 2/1995 | Neher et al. | |
| 6,448,439 B1 | 9/2002 | Eck et al. | |
| 7,179,875 B2 | 2/2007 | Fuchs et al. | |
| 7,294,741 B2 | 11/2007 | Bub et al. | |
| 7,612,230 B2 * | 11/2009 | Shima et al. .................. | 562/535 |
| 2002/0198406 A1 | 12/2002 | Karim et al. | |
| 2004/0116741 A1 | 6/2004 | Nordhoff et al. | |
| 2005/0204612 A1 | 9/2005 | Connemann et al. | |
| 2005/0222459 A1 | 10/2005 | Nordhoff et al. | |
| 2007/0129570 A1 * | 6/2007 | Shima et al. .................. | 562/538 |
| 2007/0262022 A1 | 11/2007 | Mosler et al. | |
| 2007/0274882 A1 | 11/2007 | Mosler et al. | |
| 2007/0280866 A1 | 12/2007 | Balduf et al. | |
| 2008/0091048 A1 | 4/2008 | Nordhoff et al. | |
| 2008/0119669 A1 | 5/2008 | Balduf et al. | |
| 2008/0197086 A1 | 8/2008 | Mosler | |
| 2008/0221277 A1 | 9/2008 | Walden et al. | |
| 2008/0280128 A1 | 11/2008 | Furno et al. | |
| 2008/0287616 A1 | 11/2008 | Balduf et al. | |
| 2009/0023006 A1 | 1/2009 | Bub et al. | |
| 2009/0068440 A1 | 3/2009 | Bub et al. | |

FOREIGN PATENT DOCUMENTS

| | | |
|---|---|---|
| DE | 2626887 A1 | 12/1977 |
| DE | 4238493 C1 | 4/1994 |
| DE | 10138150 A1 | 2/2003 |
| DE | 102005028624 A1 | 12/2006 |
| EP | 0534294 A2 | 3/1993 |
| EP | 0959062 A1 | 11/1999 |
| EP | 1015410 | 7/2000 |
| GB | 141057 | 6/1921 |
| JP | 2005213225 A * | 8/2005 |
| WO | 9522356 A1 | 8/1995 |
| WO | 02056812 A2 | 7/2002 |
| WO | 03051809 A1 | 6/2003 |
| WO | 2004029016 | 4/2004 |
| WO | 2006087083 A2 | 8/2006 |
| WO | 2006092272 A2 | 9/2006 |
| WO | WO 2006092272 A2 * | 9/2006 |
| WO | 2006136336 A2 | 12/2006 |

OTHER PUBLICATIONS

Furno et al., U.S. Appl. No. 11/912,011, filed Oct. 19, 2007. Furno et al., U.S. Appl. No. 12/093,548, filed May 13, 2008.
Furno et al., U.S. Appl. No. 12/280,654, filed Aug. 25, 2008.
German language version, International Search Report, mailed on Oct. 1, 2008 in PCT/EP2007/058745.
German language version, Written Opinion, mailed on Oct. 1, 2008 in PCT/EP2007/058745.
Kuppinger et al., U.S. Appl. No. 12/438,295, filed Feb. 20, 2009.
Mosler et al., U.S. Appl. No. 12/374,205, filed Jan. 16, 2009.
Walden et al., U.S. Appl. No. 12/297,822, filed Oct. 20, 2008.

* cited by examiner

*Primary Examiner* — Michael M Bernshteyn
(74) *Attorney, Agent, or Firm* — Smith Moore Leatherwood LLP

(57) ABSTRACT

The present invention relates to a process for production of acrylic acid, comprising the steps of a) dehydration of glycerine to an acrolein-comprising dehydration product; b) gas phase oxidation of the dehydration product to obtain an acrylic acid-comprising monomer gas; c) bringing into contact of the monomer gas with a quench agent to obtain an acrylic acid-comprising quench phase; and d) work-up of the quench phase to obtain an acrylic acid-comprising monomer phase; whereby, during the dehydration a liquid phase a1 and a gas phase a2 is present, whereby in the liquid phase a1 a plurality of gas bubbles is generated, as well as a process for production of polymers by polymerization of acrylic acid, preferably for production of water-absorbing polymers, the water-absorbing polymers obtainable by this process, a composite, a process for production of a composite, the composite obtainable by this process, and further chemical products.

12 Claims, 6 Drawing Sheets

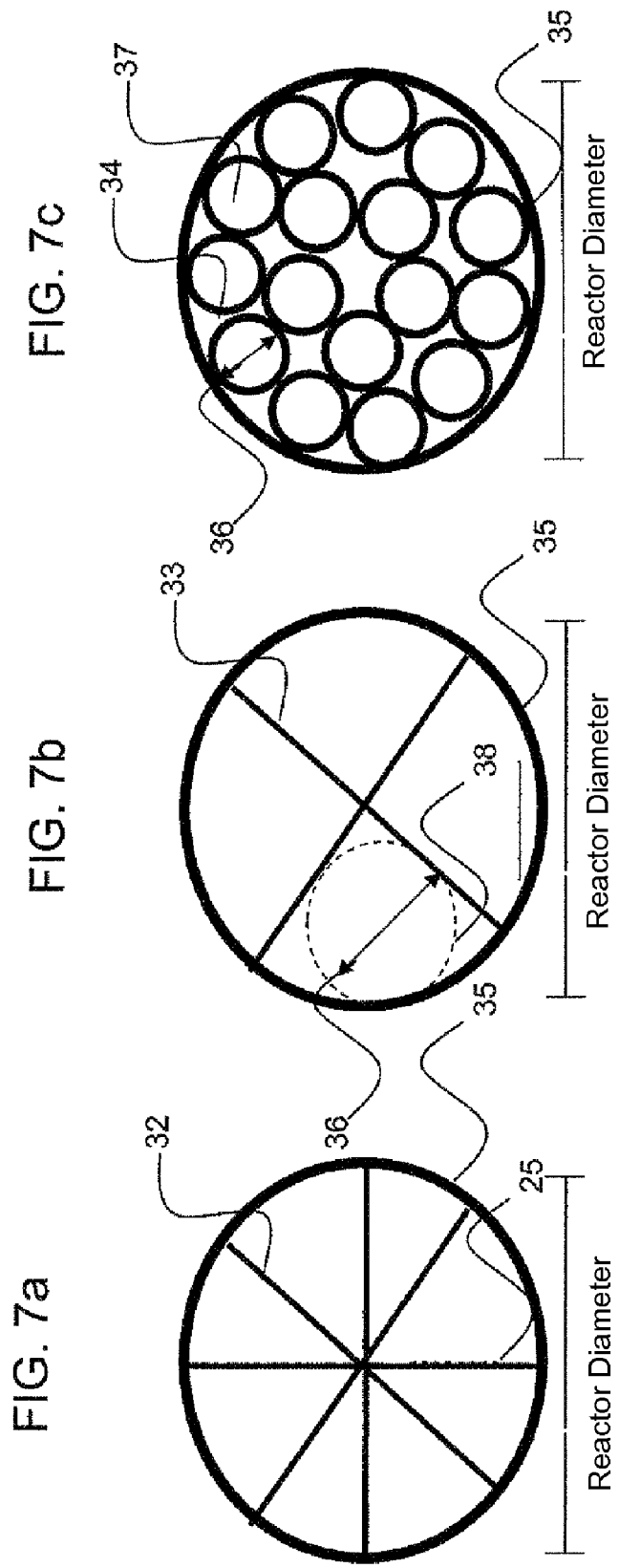

ACRYLIC ACID AND WATER-ABSORBING POLYMER STRUCTURES BASED ON RENEWABLE RAW MATERIALS AND PROCESS FOR THEIR PRODUCTION BY DEHYDRATION

This application is a national stage application under 35 U.S.C. 371 of international application No. PCT/EP2007/058745 filed 22 Aug. 2007, and claims priority to German Application No. DE 10 2006 039 205.1 filed 22 Aug. 2006, the disclosure of which is expressly incorporated herein by reference.

BACKGROUND

The present invention relates to a process for production of acrylic acid, a process for production of polymers by polymerization of acrylic acid, preferably for production of water-absorbing polymers, the water-absorbing polymers obtainable by this process, water-absorbing polymers which are based to at least 25 wt. % on partially neutralized acrylic acid, to a composite, a process for production of a composite, the composite obtainable by this process, the use of acrylic acid for production of water-absorbing polymer structures, a device for production of acrylic acid, a process for production of acrylic acid and the acrylic acid obtainable by this process.

High requirements are made of the purity of acrylic acid which is used for production of polymeric compounds. This is particularly the case if the polymers are so-called superabsorbers, which are incorporated in wound dressings or hygiene articles. These polymers are capable of absorbing and thereby binding aqueous liquids to form a hydrogel. Superabsorbers, are, therefore, particularly used in hygiene articles such as diapers, incontinence inserts, feminine hygiene articles and the like for absorption of body fluids. An encompassing over-view of superabsorbers, the application and the production is given by F. L. Buchholz and A. T. Graham (editor) in "Modern Superabsorbent Polymer Technology", Wiley-VCH, New York, 1998.

In the production of the superabsorbing polymers, generally an acrylic acid is used which has been obtained by catalytic gas phase oxidation of propylene to acrolein, which is then converted in a further catalytic gas phase oxidation to acrylic acid, subsequent absorption of the gaseous reaction mixture in water, distillation of the thus-obtained aqueous acrylic acid solution to obtain a pure acrylic acid and further purification of the crude acrylic acid by distillation or crystallization.

A disadvantage of this process for production of acrylic acid is that the reagent used (propylene) is produced from crude oil and thus from non-sustainable raw materials, which is of concern for economic aspects, above all long-term, above all with respect to the obtainment from crude oil which is becoming increasingly difficult and above all expensive.

Known superabsorbers have the disadvantage that, unless they at least partially comprise natural polymers, such as, for example, celluloses, they are hardly based on renewable raw materials. It is possible to produce many of the components used in hygiene articles, in particular in disposable diapers, from biological starting materials, but a replacement of superabsorbers based on cross-linked polyacrylates by natural superabsorbing polymers, such as, for example, by cross-linked, derivatised starches or celluloses, is generally linked with significant losses with respect to the absorbent properties. This mostly leads to considerably more of these absorbers based on natural polymers having to be used, in order to even approach the same absorbent properties in a hygiene article. This is disadvantageous, because the hygiene articles then become more voluminous and heavier, which significantly reduces wearing comfort and leads to a larger waste volume, which, in addition to more disposal space or combustion expenditure, also makes necessary increased transport capacity for the waste removal. All of this has a disadvantageous effect on the environmental tolerance of absorbers based on natural polymers.

SUMMARY

The present invention includes various embodiments set forth in the claims and including the following as taken in context with the present invention:

A process of this invention wherein the plurality of gas bubbles in the liquid phase a1 is generated by introduction of an additional gas.

A process of this invention wherein the glycerine is used in an aqueous phase.

A process of this invention wherein a dehydration catalyst is used.

A process of this invention wherein the dehydration catalyst has a $H_0$ value in a range from about +2 to about −10.

A process of this invention wherein the gas phase oxidation occurs in the presence of an oxidation catalyst comprising transition metal in elemental or chemically bound form or both.

A process of this invention wherein the dehydration product in an aqueous phase is conducted to the gas phase oxidation.

A process of this invention wherein the gas phase oxidation occurs in a temperature range from about 200 to about 400° C.

A process of this invention wherein the monomer gas comprises the acrylic acid in an amount in a range from about 5 to about 50 wt.%, respectively based on the monomer gas.

A process of this invention wherein the quench agent comprises water or an organic compound with a boiling point in a range from about 50 to about 250° C. or water and this organic compound.

A process of this invention wherein the quench phase comprises the acrylic acid in an amount in a range from about 30 to about 90 wt. %, respectively based on the monomer phase.

A process of this invention wherein the work-up occurs at temperatures below the boiling point of acrylic acid.

A process of this invention wherein the work-up occurs by extraction or crystallization or both.

A process of this invention wherein the monomer phase comprises the monomer in an amount in a range from about 25 to about 90 wt. %, respectively based on the monomer phase.

A process of this invention wherein the amount of a gas generating the plurality of gas bubbles is varied.

A process of this invention wherein the glycerine is warmed before the dehydration.

A process of this invention wherein the glycerine is warmed to a temperature in the range from about 150 to about 350° C.

A process of this invention wherein the liquid dehydration catalyst is warmed before the dehydration.

A process of this invention wherein the liquid dehydration catalyst is warmed to a temperature in a range from about 150 to about 350° C.

A process of this invention wherein the liquid dehydration catalyst is warmed separately from the glycerine.

A device of this invention wherein at least within a partial region of the dehydration reactor at least one insert which can be flowed through is provided.

A device of this invention wherein the insert which can be flowed through is formed at least in a partial region in star-, cross-, plate-, ball-, loop-, ring- or pipe-form or in at least two of these forms.

A device of this invention wherein the dehydration reactor comprises the gas bubble generator in a lower region.

A device of this invention wherein the dehydration reactor comprises an upper region narrowing to an outlet.

A device of this invention wherein at least one heat exchanger is pre-positioned to the dehydration reactor.

A process of this invention wherein the process is carried out in a device comprising
  in fluid-conducting communication with each other
  1a a dehydration reactor,
  2a a gas phase oxidation reactor,
  3a a quench unit, and
  4a a work-up unit,
  wherein the dehydration reactor comprises a gas bubble generator.

A process of this invention wherein the process is carried out in a device comprising in fluid-conducting communication with each other
  1b a dehydration reactor,
  2b a gas phase oxidation reactor,
  3b a quench unit,
  4b a work-up unit, and
  5b a polymerization unit,
  wherein the dehydration reactor comprises a gas bubble generator.

A water-absorbing polymer structure of this invention that is based to at least 25 wt. % on optionally partially neutralized acrylic acid, wherein the water-absorbing polymer structures are characterized by a sustainability factor of at least 80%.

A water-absorbing polymer structures of this invention with at least one of the following properties:
  A a Saline Flow Conductivity (SFC) determined according to the herein-described test method of more than about $30 \times 10^{-7}$ cm$^3$s/g;
  B an Absorption Against a Pressure of 0.7 psi (AAP$_{0.7}$) determined according to ERT 442.2-02 of more than about 20 g/g; or
  C a Retention (CRC) determined according to ERT 441.2-02 of at least 20 g/g.

Polymer structures of this invention wherein the polymer structures are based to at least 20 wt. %, based on the total weight of the water-absorbing polymer structures, on natural, biodegradable polymers.

Water-absorbing polymer structures of this invention comprising a plurality of inorganic fine particles.

Water-absorbing polymer structures of this invention wherein the inorganic fine particles comprise oxygen.

Water-absorbing polymer structures of this invention wherein the inorganic fine particles comprise a metal.

Water-absorbing polymer structures of this invention wherein the water-absorbing polymer structure comprises a post-crosslinked outer region.

Water-absorbing polymer structures of this invention wherein the inorganic fine particles are provided on or in or on and in the outer region.

A composite comprising a water-absorbing polymer structure of the present invention and a substrate.

A process for preparation of a composite wherein the water-absorbing polymer structures of this invention which are based to at least 25 wt. % on optionally partially neutralized acrylic acid, wherein the water-absorbing polymer structures are characterized by a sustainability factor of at least 80%, and a substrate are brought into contact with each other.

A hygiene article comprising a top-sheet, a bottom-sheet and a between-sheet arranged between the top-sheet and the bottom-sheet, which comprises water-absorbing polymer structures of this invention.

An article selected from fibers, sheets, molded articles, textile, and leather additives, flocculants, coatings, or varnishes based on acrylic acid obtainable by a process of this invention or derivatives or salts thereof.

A use of an acrylic acid obtainable by a process of this invention or derivatives or salts thereof in fibers, sheets, molded articles, textile and leather additives, flocculants, coatings or varnishes.

The present invention had as object to reduce the disadvantages arising from the prior art or even to overcome them.

The present invention includes various embodiments set forth in the claims and including the following as taken in context with the present invention:

The present invention had the object of identifying an acrylic acid production which starts from renewable raw materials and also has potential for industrial application. In this con-text, longest possible running times with little downtime, which can, for example, arise from solid deposits such as decomposition residues or polymers residues in the reactors, are meaningful.

An object was to reduce the amount of solids such as carbons or polymeric precipitates forming in the course of the operation in the production of acrolein and thus to achieve a more disruption-free operation.

In addition, an object for the present invention was to achieve, in addition to as long and disruption-free operation times as possible, also high yields with good selectivities.

The present invention also had the object of providing polymers, in particular superabsorbers, which have a particularly low content in extractable, possibly toxic components.

Furthermore, the present invention had the object of providing polymers, in particular superabsorbers, which are environmentally compatible and yet have excellent application properties. It was thus particularly desired to provide superabsorbers with improved environmental compatibility, with absorber properties remaining equally good.

In addition, an object of the present invention was to improve the environmental compatibility of the further products comprising the polymers according to the invention, such as composites in general and hygiene articles in particular, without the desired functions such as absorption capacity, wearing comfort and simplicity of production of these further products suffering.

The present invention also had the object of providing a process for production of such polymers and of the monomers suitable for their production.

In addition, an object of the present invention was to propose a process and a device for production of the monomers and/or of the polymers, which can be integrated with as little retro-fitting expenditure into existing large scale manufacturing processes and devices.

A contribution to the solution of the objects according to the invention is made by the main and additional claims, whereby the sub-claims respectively dependent thereon represent preferred embodiments of the present invention.

DETAILED DESCRIPTION

A contribution to the solution of the objects according to the invention is made by a process for production of acrylic acid at least comprising the following steps:

a. dehydration of glycerine to an acrolein-comprising dehydration product;
b. gas phase oxidation of the dehydration product to obtain an acrylic acid-comprising monomer gas;
c. bringing into contact of the monomer gas with a quench agent to obtain an acrylic acid-comprising quench phase;
d. work-up of the quench phase to obtain an acrylic acid-comprising monomer phase;

whereby, during the dehydration a liquid phase a1 and a gas phase a2 are present, whereby in the liquid phase a1 a plurality of gas bubbles is generated.

A further contribution to the solution of the above object is made by a process for production of a polymer by polymerization of acrylic acid, at least comprising the following steps:

A. dehydration of glycerine to an acrolein-comprising dehydration product;
B. gas phase oxidation of the dehydration product to obtain an acrylic acid-comprising monomer gas;
C. bringing into contact of the monomer gas with a quench agent to obtain an acrylic acid-comprising quench phase;
D. work-up of the quench phase to obtain an acrylic acid-comprising monomer phase;
E. polymerization, preferably radical polymerization, of the monomer phase;

whereby during the dehydration a liquid phase a1 and a gas phase a2 are present, whereby in the liquid phase a1 a plurality of gas bubbles is generated.

It is preferred in the process according to the invention that at least one, preferably at least two of the above steps occurs continuously and must not be successively interrupted and started again by charge-wise conversions. Preferably, at least steps a or A and b or B, and particularly preferably all steps, occur continuously.

In general, the gas bubbles in the liquid phase can be generated by any measure known to the skilled person, in one embodiment, the gas bubbles have a size in a range from 0.01 to 5 mm, preferably in a range from 0.05 to 1.5 mm and yet more preferably in a range from 0.1 to 1.2 mm. The bubble size is determined as average value of a jet in of the bubble generator used in the dehydration into water at normal pressure. To this end, through a glass sheet provided in the reactor, at least 10 snap shots of a 10 cm×10 cm region of the liquid phase a1 flowed through with gas bubbles at a distance of 20 cm from the bubble generator is prepared and the diameter of the individual gas bubbles depicted in this snap shot determined and the sum of the diameters divided by the number of gas bubbles measured.

In an embodiment of the process according to the invention, at least a part of the plurality of gas bubbles within the liquid phase a1 is conducted. The conducting should not occur only at the outer limits of the liquid phase a1 but also within the space arising from the limits of the liquid phase. In connection with the conduction of the gas bubbles, it is advantageous that at least a part of the gas bubbles, preferably at least 30% and particularly preferably at least 70% of the gas bubbles do not increase in the respective volumes.

According to a further embodiment of the process according to the invention, at least a part of the plurality of the gas bubbles within the liquid phase a1 is divided. This division can occur, for example, in that, from originally one gas bubble, two, three or more gas bubbles are formed, which are smaller in their volume than the gas bubble from which they are derived.

Further, according to another embodiment of the process according to the invention, at least a part of the plurality of gas bubbles within the liquid phase a1 is additionally slowed by the liquid phase a1. In general, the migration rate of gas bubbles in liquid depends, in addition to other factors, above all on the viscosity of the liquid. According to the invention, suitable measures are taken which lead to the gas bubbles being additionally slowed by these measures when they move upwards through the liquid phase a1. The degree of slowing of the gas bubbles by such measures provided in liquid phase a1 can be determined in that under otherwise identical conditions, gas bubbles are first conducted through the liquid, and in a further experiment through the liquid provided with the measures. In this way, the slowing influence on the rising of the gas bubbles in addition to the anyway occurring rate of migration through the liquid a1 of the gas bubbles can be determined.

As suitable measure for conducting, dividing or slowing or also for a combination of at least two thereof, in principle, all measures known and appearing suitable to the skilled person are considered. Inserts which can be flowed through and are located in the liquid phase a1 represent one of these measures. These inserts can be flowed through both by the liquid phase a1 and by the gas bubbles. By means of suitably selected measures, the migration rate of the gas bubbles through the liquid phase a1 can be adjusted and varied. These inserts can be flowed through both by the liquid phase a1 and by the gas bubbles. It is preferred for the process according to the invention that the migration rates of the gas bubbles lie in a range from 0.01 to 10 m/s, preferably in a range from 0.1 to 5 m/s and particularly preferably in a range from 0.1 to 2.5 m/s. The migration rate of the gas bubbles is given as average migration rate. This can be determined by the generation of corresponding gas bubbles in a glass cylinder comprising the liquid phase a1 by determination of individual migration rates of 100 gas bubbles by the sum of the individual migration rates divided by the number of gas bubbles.

The above mentioned measures for control of the residence time of the gas bubbles serve to achieve as high as possible an acrolein discharge from the dehydration reactor in addition to as high as possible an acrolein saturation in the gas bubbles. It is furthermore often desirable that the inserts contribute to a reduction of the back-mixing within the dehydration reactor in operation. The above measures contribute hereto themselves and in a combination of at least two thereof. It can be desirable in this context and depending on the construction design of the dehydration reactor to combine two or more measures having opposing effects with each other.

In an embodiment of the present invention, the generation of the gas bubbles occurs by introduction of an inert gas into the liquid phase a1. As inert gas, in principle all inert gases known to the skilled person are considered. The inert gas should be selected such that it hardly reacts, or, better, not at all, with the chemicals taking part in the dehydration. Furthermore, in the selection, it should be taken into account that the dehydration product and preferably acrolein can absorb well the gas or the gases for the gas bubble gas or additional gas. As gases for the generation of gas bubbles, preferably gases with a content of at least 10 vol. %, preferably at least 50 vol. %, and particularly preferably at least 80 vol. %, respectively based on the additional gas, air, $CO_2$, $N_2$ or water vapor or a mixture of at least two thereof and particularly preferably $N_2$ and water vapor and yet more preferably $N_2$ come into consideration. It is preferred that as much as possible of the liquid phase a1 is flowed through by gas bubbles. In this way, it can be achieved that the dehydration product is transferred out of the liquid phase a1 into the gas phase a2. This can occur by a process also known as "stripping". Afterwards, the dehydration product is taken up by the gas, also described as carrier gas, into the gas bubbles, and transferred out of the liquid phase a1 into the gas phase a2 and—if necessary—the dehydration product brought back into liquid form. In this way, it is achieved that the concentration of dehydration product in the gas phase is higher than in the liquid phase. It is preferred that the content of glycerine in the gas phase is above that of the liquid phase by at least 1.5 times, preferably at least 3 times and particularly preferably at least 5 times.

By the taking up of the dehydration product into the gas bubbles and by the gas bubbles leaving the liquid phase a1 as quickly as possible, a discharge of the dehydration product from the liquid phase a1 with as little back-mixing as possible is achieved. In this way, by means of the plurality of gas bubbles, the acrolein arising in the dehydration is transferred out of the liquid phase a1 into the gas phase a2. This can be conducted, still in the gaseous state, to the gas phase oxidation. In general, this occurs after a reactor residence time (residence time=volume flow/reactor volume) in a range of from 1 to 30 minutes, preferably in a range of from 2 to 20 minutes and particularly preferably in a range of from 5 to 15 minutes.

In an embodiment of the process according to the invention, it is preferred that the glycerine has been obtained by saponification of fats. These fats can be both animal as well as vegetable fats. Animal fats accumulate in particular in animal body recycling. Vegetable fats are obtained in large amounts in oil extraction from oily fruits such as rape, soya, sesame, olives and sunflower seeds. Large amounts of glycerine are obtained in particular in a production of so-called "biodiesel" from rape oil, as can be seen in WO-A-2004/029016, among others. Accordingly, it is preferred in the process according to the invention that the glycerine accumulates in the generation of liquid carburants from natural raw materials. This is given in particular with saponification devices connected after oil mills.

In the process according to the invention, it is further preferred that the dehydration occurs along a path over which the glycerine concentration decreases. As path, as a rule, the longitudinal direction of the reactor used for dehydration comes into consideration. In general, the path begins at the entrance of the reagent into the reactor and ends with the product outlet of the reactor. It is thus further preferred in the process according to the invention that along this path a pressure change occurs. In some cases, the pressure at reagent entry is higher than the pressure at reagent exit. The reagent entry pressure is, in these cases, preferably in a range from 1 to 300 mbar, preferably in a range from 10 to 200 mbar and particularly preferably in a range from 20 to 120 mbar higher than the pressure at the product exit. It is furthermore preferred in the process according to the invention that the dehydration occurs along a path over which the glycerine concentration decreases, whereby it is preferred that along this path different flow rates exist. It is, thus, preferred that the flow rate at the reagent entry is lower than at the product exit. The above measures are advantageous for the continuous operation of the process according to the invention.

In an embodiment of the process according to the invention, it is preferred that the dehydration at least partially occurs in liquid phase. As liquid phase, in particular aqueous systems are preferred. If the dehydration is carried out at least partially or even fully in a liquid phase, this has the advantage, in particular if this is an aqueous phase, that with high glycerine concentrations, high acrolein concentrations in the aqueous phase can be achieved, which can be discharged by means of the gas bubbles as quickly as possible. These aqueous phases with high acrolein concentrations can be used directly in the next step of the gas phase oxidation. The further advantage of the liquid phase dehydration is that a rinsing effect can be achieved by means of the liquid phase, with which a formation of deposits in the reactor can be significant reduced, which leads to higher reactor running times and thus to a reduced necessity for regeneration of the reactor.

In general, the dehydration can occur at a temperature in a range from 100 to 400° C., preferably in a range from 130 to 350° C. and particularly preferably in a range from 150 to 330° C. A further advantage of the liquid phase dehydration is that this can be carried out at relatively moderate temperatures, in a range from 160 to 310° C., preferably in a range from 200 to 300° C. and yet more preferably in a range from 250 to 290° C. These temperature ranges mostly lie, with increased pressures, considerably under the decomposition and boiling temperature determined at normal pressure for glycerine of about 290° C., which leads to reduction of decomposition residues and polymers as well as other impurities, which have a disadvantageous effect on the operational duration of the gas phase oxidation. It is preferred in the liquid phase dehydration that this occurs in a cyclical way, in which the glycerine-containing liquid phase is conducted by means of a pump to the reactor designed as a pressure system and comprising a catalyst. In this way, in a gentle way, in addition to a higher selectivity, higher turnovers and considerably fewer side products can be obtained.

In another embodiment of the process according to the invention, it is preferred that at least the gas used for generation of the gas bubbles in the reactor, after leaving the reactor, is at least partially, for example to at least 1 vol. %, preferably to at least 10 vol. % and particularly preferably to at least 30 vol. %, fed back into the reactor for renewed generation of gas bubbles. This can occur by means of a cycling gas operation mode, in which the gas, after at least partial separation of the acrolein as dehydration product, is fed into the dehydration reactor again. Separately, or also together with this gas, at least a part, for example to at least 1 vol. %, preferably to at least 10 vol. % and particularly preferably at least 30 vol. % of the glycerine not converted in the dehydration can be fed into the dehydration reactor again. In addition, it is preferred that the aqueous phase at least partially freed from the dehydration product is also at least partially, for example to at least 1 vol. %, preferably to at least 10 vol. % and particularly preferably to at least 30 vol. %, fed into the dehydration reactor again and thus conducted in the cycle. Furthermore, the above-described conductings back into the reactor can occur alone or in combination of at least two, whereby it is preferred that all three above-described conductings back are carried out.

In a further embodiment of the process according to the invention, it is additionally also possible that the dehydration at least partially or also completely occurs in a gas phase. The dehydration in gas phase has proven itself in particular in a conversation of glycerine from fat saponification. This glycerine generally conducts a high salt charge with it, which can be separated very well by the vaporization step of the gas phase dehydration. As also in the liquid phase dehydration, it also preferred in the gas phase dehydration that this occurs in the presence of water.

As a result, it is preferred in the process according to the invention that the glycerine is used in an aqueous phase. In the case of the liquid phase dehydration, this liquid glycerine phase generally comprises a water content in the range from 0 to 30 wt. %, preferably in a range from 0 to 20 wt. % and particularly preferably in a range from 0 to 10 wt. % water, respectively based on the aqueous phase. In the case of the gas phase dehydration, the aqueous glycerine phase generally comprises a water amount in a range from more than 30 to 97 wt. %, preferably in a range from 60 to 95 wt. % and yet more preferably in a range from 70 to 90 wt. %, respectively based on the aqueous glycerine phase. The further main component of the glycerine phase is glycerine.

The dehydration can occur in principle at any pressures appearing suitable to the skilled person. It is, however, preferred that the dehydration occurs at a pressure in a range from 2 to 200 bar, preferably 10 to 150 bar and particularly preferably in a range from 15 to 70 bar. It is, furthermore, advantageous to maintain certain temperature and pressure ranges in the dehydration.

According to another embodiment of the process according to the invention, it is preferred to combine a liquid dehydration and gas phase dehydration with each other. According to a form of the process according to the invention, the glycerine can first be conducted to the gas phase dehydration and then to the liquid phase dehydration or the other way round. In the first-mentioned order, there is the advantage that glycerine charges arising from fat saponification which are heavily loaded with salt can first be liberated from this salt charge by an evaporation in the gas phase dehydration, in order to then be subsequently further converted in the liquid phase dehydration by means of the cyclic operation mode, to high yields and selectivities with few side products.

According to a further embodiment of the process according to the invention, a dehydration catalyst is used in this process. As dehydration catalysts both acidic as well as alkaline catalysts can be considered. Acidic catalysts are preferred in particular because of the low tendency to form oligomers. The dehydration catalyst can be used both as homogenous and as heterogeneous catalyst. If the dehydration catalyst is present as heterogeneous catalyst, it is preferred that the dehydration catalyst is in contact with a carrier x. As carrier x. all solids appearing suitable to the skilled person can be considered. In this context, it is preferred that these solids have suitable pore volumes, which are suitable for good binding and taking up of the dehydration catalyst. In addition, total pore volumes according to DIN 66133 in a range from 0.01 to 3 ml/g are preferred and in a range from 0.1 to 1.5 ml/g particularly preferred. In addition, it is preferred that the solids suitable as carrier x. have a surface area in a range from 0.01 to 1000 m$^2$/g, preferably in a range from 0.005 to 450 m$^2$/g and yet more preferably within a range from 0.01 to 300 m$^2$/g according to BET test according to DIN 66131. As carrier for the dehydration catalyst, on the one hand a bulk material which has an average particle size in a range from 0.1 to 40 mm, preferably in a range from 1 to 10 mm and yet more preferably in a range from 1.5 to 5 mm can be used. Furthermore, the wall of the dehydration reactor can act as carrier. Furthermore, the carrier can itself be acidic or basic, or an acidic or a basic dehydration catalyst can be applied to an inner carrier. As application techniques should be mentioned in particular immersion and/or impregnation or the incorporation into a carrier matrix.

As carrier x., which can also have dehydration catalyst properties, in particular natural or synthetic silicate materials, such as, in particular, mordenite, montmorillonite, acidic zeolites; carrier materials charged with mono-, di- or polybasic inorganic acids, in particular phosphoric acid or acidic salts of inorganic acids, such as oxidic or silicate materials, for example, $Al_2O_3$, $TiO_2$; oxides and mix oxides, such as, for example, gamma-$Al_2O_3$ and ZnO—$Al_2O_3$ mixed oxides or the heteropolyacids are particular suitable.

According to another embodiment according to the invention, the carrier x. consists at least partially of an oxidic compound. Such oxidic compounds should comprise at least one of the elements Si, Ti, Zr, Al, P or a combination of at least two thereof. Such carriers can also work themselves as dehydration catalyst by means of their acidic or basic properties. A preferred class of compounds with effect both as carrier x. as well as dehydration catalyst comprise silicone oxides, aluminum oxides, phosphorus oxides. Preferred basic materials acting both as dehydration catalyst and as carrier x. comprise alkaline, alkaline earth, lanthanum, lanthanide metal or a combination of at least two thereof in their oxidic form. Such acidic or basic dehydration catalysts are commercially obtainable both from Degussa AG and from Südchemie AG. Ion exchanges represent a further class. These can also be present in both basic and in acidic form.

As homogenous dehydration catalysts, in particular inorganic acids, preferably phosphorus-comprising acids and yet more preferably phosphoric acids are considered. These inorganic acids can be immobilized on the carrier x. by immersion and/or impregnation. Another group of interesting homogenous catalysts are sulphur-containing acids such as sulphurous acid or sulphuric acid or a mixture thereof.

In particular with the gas phase dehydration, the use of heterogeneous catalysts has particularly proven itself. In the liquid phase dehydration, however, both homogenous as well as heterogeneous dehydration catalysts are used.

In addition, it is preferred that in the process according to the invention, a dehydration catalyst with a $H_0$-value in a range from +1 to −10, preferably within a range from +2 to −8.2 and yet more preferably in the liquid phase dehydration in a range from +2 to −3 and in the gas phase dehydration in a range from −3 to −8.2 is used. The $H_0$-value corresponds to the Hammett acid function and can be determined by the so-called amine titration and use of indicators, or by absorption of a gaseous base—see "*Studies in Surface Science and Catalytics*", vol. 51, 1989: "*New solid Acids and Bases*, their catalytic Properties", K. Tannabe et al. Further details for the production of acrolein from glycerine can further be taken from DE 42 38 493 C1.

In a further embodiment of the process according to the invention, the gas phase oxidation in step b) of the process according to the invention occurs in the presence of one or more oxidation catalysts, which comprise transition metals in elemental or chemically bound form or both. With the oxidation catalysts, it is preferred that these comprise at least one of the elements molybdenum, tungsten or a combination of at least two thereof in at least partially oxidized form. Such oxidation catalysts are preferably used as heterogeneous catalyst in contact with a carrier y. It is in this case preferred that the oxidation catalysts are incorporated into the carrier y. As suitable carrier y., in principle, the compounds mentioned in connection with the carrier x. are considered, whereby carriers on the basis of silicon oxide or aluminum oxide or aluminum-silicon oxide are particularly preferred. Such oxidation catalysts are described in detail in the literature. Reference is made in this context, for example to DE-A-26 26 887, EP-A-0 534 294 and to US-A-2002/0198406. Such oxidation catalysts for the conversion of acrolein to acrylic acid are commercially obtainable, for example from Mitsubishi Corp., Japan.

It is further preferred in the process according to the invention that the dehydration product in an aqueous phase is conducted to the gas phase oxidation. It is here preferred that the dehydration product comprises at least 10 wt. %, preferably at least 20 wt. % and yet more preferably at least 40 wt. % acrolein. The water amount should lie in a range from 0.1 to 50 wt. %, preferably in a range from 10 to 40 wt. % and yet more preferably in a range from 12 to 20 wt. %, whereby these, and the above wt. % details are respectively based on the phase fed into the gas phase oxidation.

The gas phase oxidation is preferably carried out in a temperature range from 200 to 400° C., preferably in a range from 250 to 350° C. and yet more preferably in a range from 280 to 340° C.

It is further preferred in the process according to the invention that the monomer gas comprises the acrylic acid in an amount in a range from 5 to 50 wt. %, preferably in a range from 10 to 40 wt. % and yet more preferably in a range from 15 to 30 wt. %, respectively based on the monomer gas.

In a further embodiment of the process according to the invention, it is preferred to use water or an organic compound with a boiling point in a range from 50 to 250° C., preferably in a range from 70 to 180° C. and yet more preferably in a range from 105 to 150° C. or water and this organic compound quench agent in process step c) of the process according to the invention. As such organic compound, in particular aromatics and yet more preferably alkylated aromatics are considered. Generally, the quench agent is brought into contact with the monomer gas in a suitable column, preferably in counter flow. For the case that the quench agent consists to at least 50 wt. %, preferably at least 70 wt. % of water, it is preferred that the aqueous quench agent loaded with acrylic acid is worked up in a further step with a separating agent, which is preferably not well soluble with water. The phase richest in acrylic acid is subjected either to a distillation or to a crystallization or to both, preferably first to a crystallization. The crystallization can be carried out both as layer as well as suspension crystallization. Suitable layer crystallization devices are commercially obtainable from Sulzer AG. Suitable suspension crystallization devices generally make use of a crystal generator followed by a wash column. Such devices and processes are commercially obtainable from Niro Prozesstechnologie BV. As extraction/separating agent, in particular an aromatic compound, yet more preferably an alkyl aromatic and more preferably toluene are considered. Should an organic compound be used as separating agent, this organic compound charged with acrylic acid can likewise be subjected both to a distillation as well as to a crystallization or to a combination of both. A crystallization suitable for this is disclosed in EP-A-1 015 410.

In addition, it is preferred in the process according to the invention that the quench phase comprises the acrylic acid in an amount in a range from 30 to 90 wt. %, preferably in a range from 35 to 85 wt. % and yet more preferably in a range from 45 to 75 wt. %, respectively based on the monomer phase.

In a further embodiment of the process according to the invention, it is preferred that the work-up of the quench phase occurs at temperatures below the boiling point of acrylic acid. A suitable measure for this is that the quench phase already has a temperature of below 40° C. by use of a correspondingly cold quench agent. The thus temperature controlled quench phase can then be conducted to an extraction or crystallization or both for work-up, whereby the temperatures preferably lie in a range from −40 to 40° C., preferably in a range from −20 to 39° C. and particularly preferably in a range from −10 to 35° C.

According to a further embodiment of the process according to the invention, it is preferred that the monomer phase comprises the acrylic acid in an amount in a range from 99 to 99.98 wt. %, respectively based on the monomer phase. Such acrylic acid contents in a monomer phase occurred in particular if the work-up occurs by distillation. For the case that the work-up occurred by extraction and crystallization, it can be preferred that the acrylic acid is present in the monomer phase in an amount from 30 to 70 wt. %, preferably in an amount in a range from 40 to 60 wt. % and yet more preferably in an amount in a range from 45 to 65 wt. %, in addition to water, and the impurities which are different from water and acrylic acid amount to less than 0.02 wt. %, based on the monomer phase. This aqueous monomer phase has the advantage that it can be used, without further dilution steps, as is necessary with the highly concentrated monomer phase, in the aqueous polymerization of the monomer phase.

According to another embodiment of the process according to the invention, the amount of a gas generating the plurality of gas bubbles is varied. This variation occurs over time. It is, thus, preferred that the gas amount is checked at least one time per second and increased or decreased by at least 1 vol. % according to the requirements of the process according to the invention. With uniform process operation, the variation intervals can also occur longer, for example in 1 to 100-minute intervals. By variation of the gas amounts, the yields can be controlled, for example by the gas bubble density and size. Furthermore, by means of this variation, the composition, type and quality of the reagents used can be reacted to flexibly. Furthermore, by the variation of the gas amount, the concentration of the acrolein to be further converted in the gas phase oxidation reactor can also be controlled, so that also here optimal reaction conditions can be set.

It corresponds to further embodiment of the process according to the invention that the glycerine is warmed before the dehydration. This can occur, preferably in that the glycerine is warmed before entry into the dehydration reactor. This warming preferably occurs in such a way that the pre-warmed glycerine is fed into the dehydration reactor. It is preferred that the glycerine is warmed to a temperature in a range from 150 to 350° C., preferably in a range from 250 to 310° C. and particularly preferably in a range from 270 to 290° C. Not only in the case of the pre-warming of the glycerine, but also generally in connection with the process according to the invention, it is preferred that a liquid dehydration catalyst is used, preferably phosphoric acid or sulphuric acid. Furthermore, it is preferred in another embodiment of the process according to the invention that the liquid dehydration catalyst is warmed before the dehydration. This can occur together with the glycerine, it is, however, preferred that the liquid dehydration catalyst is warmed separately from the glycerine. The liquid dehydration catalyst is preferably warmed to a temperature in a range from 150 to 350° C., preferably in a range from 250 to 310° C. and particularly preferably in a range from 270 to 290° C.

In addition, the invention relates to a device for production of acrylic acid which comprises the following components in fluid-conducting communication with each other:
1a. a dehydration reactor;
2a. a gas phase oxidation reactor;
3a. a quench unit;
4a. a work-up unit;
whereby the dehydration reactor comprises a gas bubble generator.

In addition, the invention relates to a device for production of polymers which comprises, in fluid-conducting communication with each other, firstly the above-detailed components 1a. to 4a. and furthermore a polymerization unit 5b.

By fluid-conducting is understood a communication of the individual components or the components by pipe work systems or other transport possibilities for gases and liquids, such as tank vehicles.

It is preferred in the device according to the invention that the dehydration reactor comprises a reagent container suitable for take-up of glycerine, followed by a reaction area designed for take-up of catalyst, in turn followed by a quencher formed as heat exchanger with an outlet to the gas phase oxidation reactor, whereby between the outlet and the gas phase oxidation reactor the separator for separation of gaseous and liquid components as well as optionally a distillation column for purification of the liquid phase accumulating in the separator are provided as separation unit. These components are formed from common materials which are used for the chemical industry and which are inert in connection with reaction conditions, such as stainless steel or glass. In the lower half of the reactor, one or at least two gas bubble generators are provided, which is preferably formed as a fritte, which mostly consists of metal. For the case that the reaction area comprises the catalyst as bulk product, this comprises corresponding containers. In another embodiment, the reaction area can also comprise walls which function as catalyst. Should a liquid catalyst be used in addition to or instead of the solid catalyst, it is preferred also to store this in a tank. In a preferred embodiment of the process according to the invention, at the dehydration reactor is connected a heat exchanger, in which the gas coming from the dehydration reactor is cooled. A further embodiment provides that after the dehydration reactor and before the gas phase oxidation reactor, a phase separation container follows indirectly or directly, in which a liquid phase with more acrolein than in the likewise there-comprised gas phase accumulates. This acrolein-poor gas phase can be fed into the gas phase oxidation reactor for regulation of the gas amounts and thus of the concentration ratios. It further corresponds to an embodiment that between dehydration reactor and gas phase oxidation reactor a thermal separating unit is arranged, which is preferably formed as distillation column. In this thermal separating unit, acrolein as low-boiler is separated from high-boilers and also glycerine, whereby the glycerine is conducted again to the dehydration reactor. The thus-obtained, purified acrolein pre-sent as gas phase is, optionally conducting yet further gaseous components with it, then conducted to the gas phase oxidation reactor. In another embodiment, downstream of the dehydration reactor, the heat exchanger and the phase separation container and thermal separating unit are arranged before the gas phase oxidation reactor. In another embodiment of the device according to the invention, this comprises an inert gas conduit, with which, on the one hand, the gas is fed in for generation of the gas bubbles in the dehydration reactor, and, on the other hand, gas is fed into the gas phase oxidation reactor.

In a further embodiment of the device according to the invention, it is preferred that at least within a partial region of the dehydration reactor at least one insert which can be flowed through is provided. It is further preferred that the insert which can be flowed through is formed at least in a partial region in star-, cross-, plate-, ball-, loop-, ring- or pipe-form or in at least two of these forms, whereby plate- and pipe-forms are preferred and pipe-forms are particularly preferred. In connection with the insert which can be flowed through, reference is first made to the details here concerning the conducting, division and slowing the gas bubbles.

Furthermore, as inserts which can be flowed through, all designs known to the skilled person and appearing suitable are considered in principle, such as plates, honeycombs, rings, meshes, tubes or combinations thereof. The inserts can be formed both as elements, as well as connected fixed or in one piece with the dehydration reactor. Furthermore, the inserts which can be flowed through suitable according to the invention can also be formed from the reactor wall of the dehydration reactor. This can be accomplished, for example, by means of protuberances of the reactor wall projecting into the inner space of the dehydration reactor. By this design and dimensioning of the through-flow spaces of the insert which can be flowed through, both the size as well as the rate of flowing through of the gas bubbles in the liquid phase a1 can be regulated. It is generally the case that the size of the gas bubbles is determined by the respective flow cross-section of the spaces flowed through of the insert which can be flowed through. This can be determined in that in an insert cross-section corresponding to the cross-section of the dehydration reactor a circle, which comes closest to the cross-section of the gas bubbles, is placed in such a way that this circle abuts tangentially at least three places of the insert cross-section and the flow cross-section is double the radius of this circle. In general, the flow cross-section of the insert is selected at least as large as the gas bubble diameter to be set. Accordingly, it is preferred that at least in a region of the flowed-through space the flow cross-section lies in a range from 0.1 to 100 mm, preferably from 1 to 70 mm, and yet more preferably in a range from 5 to 40 mm.

Furthermore, the migration rate and thus the residence time of the gas bubbles and the gas amount in the liquid phase a1 can also be influenced by the surface properties of the units which can be flowed through, in particular if this is in contact with the gas bubbles and the liquid phase a1. For this, in particular rough surfaces are particular suitable, whereby the roughness of the surfaces is adapted to the composition of the liquid phase a1 and the gases comprised in the gas bubbles.

Inserts which can be flowed through are preferably separating plates, in particular arranged parallel, cross-, dash-, or star-formed, two or more pipes, meshes, interlaced materials, rings, chains, bowls, in particular hollow bowls or brushes, preferably arranged bundle-like in the reactor, or a combination of two or more of the above listed possible insert variants. The inserts which can be flowed through can also be formed, in principle, from all materials known to the skilled person for this and appearing suitable. As materials are preferred in particular ceramic, glass and steel. It is important in the selection of the suitable material that this is as resistant as possible to the conditions during the dehydration reaction. Accordingly, particularly preferred are steel pipe bundles, meshes, such as, for example, the brush-like formed longitudinal wire meshes offered by Cal Gavin Ltd., ceramic and/or glass rings, as are used, for example, in distillation columns and known as Raschig rings.

Corresponding to a further embodiment according to the invention, the inserts which can be flowed through only take in a part of the dehydration reactor. This is preferably the part in which the liquid phase a1 is also located during the reaction. In addition, it is preferred that the inserts which can be flowed through are provided offset to the gas bubble generator. Relative to the central axis of the dehydration reactor in the longitudinal direction, it is preferred that the inserts which can be flowed through take in between 5 and 95%, preferably between 50 and 90% and particularly preferably between 70 and 85% of the total length of the dehydration reactor based on this axis. It is further preferred that, relative to the longitudinal axis seen in the flow direction, fewer units which can be flowed through are provided in the flowing in as well as in the flowing out region of the dehydration reactor as in the reaction region located between the flowing in and flowing out region.

In a further embodiment of the device according to the invention, it is preferred that the dehydration reactor comprises an upper region narrowing to an outlet. This narrowing can occur both linearly as well as bent or in a combination of linear and bent. In the case of the bent narrowing, this bending can be concave or convex. Often, the narrowing can be formed conically as well as partially spherically. In the case of the conical embodiment, the narrowing is substantially in blunt conical form. In principle, the skilled person designs the narrowing so that the gases arising from the liquid phase lying below the narrowing in operation of the reactor are accelerated on flowing through the narrowing. It is furthermore possible that, in addition to the gases, the liquids discharging via the narrowing are also accelerated. In a further embodiment, it is preferred that a broadening occurs again after the narrowing, in which the gases flowing through are decelerated.

Furthermore, it is preferred in an embodiment of the device according to the invention that a heat exchanger is pre-positioned to the dehydration reactor. It is preferred that the heat exchanger or exchanges are arranged so close to the dehydration reactor that no significant cooling can occur between heat exchanger and dehydration reactor. Preferably, at least, one heat exchanger is provided for the glycerine as reagent and for the liquid catalyst. For the case that no liquid catalyst is used, it is sufficient to provide a heat exchanger in the device according to the invention to the glycerine.

A further development of the device according to the invention comprises, after the reagent container and before the reaction area, an evaporator. These embodiments are particularly suitable for the gas phase dehydration. For the case that the glycerine from fatty acid saponification with a high salt load is used, it is preferred that the evaporator comprises a salt separator.

As gas bubble generator, in general any device appearing suitable to the skilled person can be used. It is preferred that the gas bubble generator is arranged in the lower half of the reactor, so that as advantageous and complete as possible a flowing through of the liquid phase in the dehydration reactor can be achieved. Suitable gas bubble generators, are, for example, frittes made of metal or glass out of which the gas bubbles bead, injectors, which can be directed against a deflector, or injectors working according to the Venturi-principle. The injectors can also be combined with a statistical mixer, which fragments the gas stream out of the injector into small gas bubbles and distributes these as homogenously as possible in the reactor.

As gas phase oxidation reactors, all reactors known to the skilled person appearing suitable for the process according to the invention can be considered which are capable of converting acrolein by gas phase oxidation to acrylic acid. Preferred in this context are multitube reactors or plate reactors which are cooled with a cooling agent, preferably with a molten salt. These multitube or plate reactors take up a suitable catalyst on the sides facing away from the cooling agent. This can be present on the one hand as powder bed and on the other hand, the surfaces of the pipes and/or of the plates can be coated with the catalyst.

As quench units, the common types in the previous large scale gas phase oxidation of acrolein to acrylic acid are likewise preferably used. Such quench units are formed columns or towers and can, exactly as for the reactors, be commercially obtained, for example, from Deggendorfer Werft GmbH. As work-up unit, likewise all known distillation and crystallization as well as extraction devices known to the skilled person from the large scale synthesis of acrylic acid via gas phase oxidation of acrolein can be considered.

As polymerization units, which are used in process step E. for polymerization of the monomer phase, on the one hand, discontinuously operating stirrer vessels and on the other hand continuously operating systems, such as belt polymerization devices, extruders and the like are suitable. A comminution and drying follows these polymerization reactors. The thus-obtained superabsorber precursor can further be subjected to a surface- or post-crosslinking. More details are found in the above-mentioned work from Graham & Buchholz. If the polymers are crosslinked, partially neutralized polyacrylates, reference is made concerning the exact procedure to the 3rd chapter (page 69 et seq.) in "Modern Superabsorbent Polymer Technology", F. L. Buchholz and A. T. Graham (editor) in Wiley-VCH, New York, 1998, which forms a part of the disclosure.

In addition, it is preferred that the process according to the invention for production of acrylic acid and the process according to the invention for production of a polymer occurs using the devices described above and more closely illustrated in the figures.

In this way, water-absorbing polymer structures as particularly suitable superabsorbers can be obtained.

A contribution to the solution of the above-mentioned object is also made by water-absorbing polymer structures obtainable by radical polymerization of the acrylic acid obtainable by the above-described synthesis process in the presence of crosslinkers.

A contribution to the solution of the above-mentioned objects is also made by water-absorbing polymer structures which are based to at least 25 wt. %, preferably to at least 50 wt. %, yet more preferably to at least 75 wt. % and most preferably to at least 95 wt. % on acrylic acid, whereby the water-absorbing polymer structures are characterized by a sustainability factor of at least 80%.

The sustainability factor indicates to what proportion the polymer structure is based on materials based on non-fossil, renewable organic material. With a sustainability factor of 100, the polymer structure consists entirely of non-fossil, renewable organic material based materials.

Another embodiment according to the invention corresponds to a water-absorbing polymer structure which is based to at least 25 wt. %, preferably to at least 50 wt. %, yet more preferably to at least 75 wt. % and most preferably to at least 95 wt. % on acrylic acid, whereby at least 80 wt. % and most preferably at least 95 wt. % of the acrylic acid monomers used for production of the water-absorbing polymer structures have been obtained by a synthesis process which starts from non-fossil, renewable organic material. Non-fossil, renewable organic materials are, in particular, not materials obtained from petroleum, or coal and/or brown coal or natural gas. Rather more, these non-fossil, renewable organic materials are products of agriculture and forestry, in particular fats and oils from glycerine and fatty acids. Preferably, these water-absorbing polymer structures are obtainable by a process comprising the following process steps:
i) polymerization of the acrylic acid in the presence of a crosslinker to form a polymer gel;
ii) optionally comminution of the polymer gel;
iii) drying of the optionally comminuted polymer gel to obtain water-absorbing polymer structures, and
iv) optionally surface post-treatment of the water-absorbing polymer structures.

According to a particular embodiment of the water-absorbing polymer structures according to the invention, these are based to at least 20 wt. %, preferably to at least 35 wt. % and most preferably to at least 45 wt. % on natural, biodegradable polymers, preferably on carbohydrates such as, for example, celluloses or starches.

In connection with the water-absorbing polymer structure according to the invention, it is preferred that this has the following properties:
A a Saline Flow Conductivity (SFC) determined according to the test method described herein of more than $30 \times 10^{-7}$ cm$^3$s/g, preferably of more than $60 \times 10^{-7}$ cm$^3$s/ g, particularly preferably of more than $90\times10^{-7}$ cm³s/g and further preferably of more than $120\times10^{-7}$ cm³s/g as well as further preferably of more than $130\times10^{-7}$ cm³s/g and most preferably of more than $140\times10^{-7}$ cm³s/g;

B an Absorption Against a Pressure of 0.7 psi ($AAP_{0.7}$) determined according to ERT 442.2-02 of more than 15 g/g, preferably of more than 16 g/g, preferably of more than 17 g/g, particularly preferably of more than 19 g/g and further preferably of more than 20 g/g as well as most preferably of more than 22 g/g;

C a Retention (CRC) determined according to ERT 441.2-02 of more than 20 g/g, preferably of more than 21 g/g, preferably of more than 22 g/g, particularly preferably of more than 23 g/g and further preferably of more than 25 g/g as well as most preferably of more than 27 g/g.

It is also possible to provide upper limits for the properties such as SFC, AAP and CRC. Such upper limits lie, for SFC in some cases at $180\times10^{-7}$ cm³s/g or at $200\times10^{-7}$ cm³s/g and sometimes also at $250\times10^{-7}$ cm³s/g or at $350\times10^{-7}$ cm³s/g or also $500\times10^{-7}$ cm³s/g. Upper limits for AAP lie at 30 g/g, in some cases at 35 g/g and sometime at 45 g/g. Upper limits for CRC are at 35 g/g, in some cases at 45 g/g and sometimes at 50 g/g.

It is further preferred that the water-absorbing polymer structure according to the invention in addition to the properties A to C further has the following:

D a biodegradability determined according to the modified Sturm-test according to appendix V to Guideline 67/548/EEC after 28 days of at least 25%, preferably at least 35% and most preferably at least 45%, whereby a value of at most 75 to 95% as upper limit is in general not exceeded.

It is further preferred that the water-absorbing polymer structure according to the invention comprises a plurality of inorganic fine particles. As inorganic fine particles, all water-insoluble inorganic compounds can be used out of which stable, colloid-disperse, preferably one phase, aqueous solutions can be obtained, which show no phase separation, such as, for example, the precipitation of a solid, inorganic precipitate, at 20° C. and normal pressure over a time period of at least 6 h, preferably at least 24 h and particularly preferably at least 72 h up to 6 months.

By a colloid disperse solution is preferably understood a solution which comprises particles with a particle diameter in a range from 100-1000 Å($10^{-4}$ to $10^{-5}$ cm). These solutions have the property of scattering in all directions a beam of light passed through the solution, so that the course of the light beam through the colloid disperse solution can be followed (Tyndall Effect, see Hollemann-Wilberg, Lehrbuch der anorganischen Chemie, 91.-100. edition, de Gruyter-Verlag, page 765).

In connection with the water-absorbing polymer structures according to the invention, it is preferred that the inorganic fine particles comprise oxygen. It is further preferred that the inorganic fine particles comprise a metal.

As particularly preferred colloid disperse inorganic compound, in the process according to the invention, particles comprising polysilicic acid are used. A colloid disperse solution comprising such particles (silica sol) can be obtained, for example, by careful acidification of sodium silicate solutions which react as alkalis as a result of hydrolysis, or by dissolving molecular silicic acid in water and optionally subsequent stabilization of the arising colloid disperse solution. The exact production of such silica sol is known to the skilled person and is described, for example, in Jander-Blasius, "Lehrbuch der analystischen und präparativen anorganischen Chemie" S. Hirzel Verlag, Stuttgart. In addition to the colloid disperse silicic acid, according to the invention, iron(III) oxide hydrate sols, tin(IV) oxide hydrate sols or sols based on silver halides, in particular silver chloride, are further particularly preferred as colloid disperse inorganic compound.

The water-absorbing polymer structures according to the invention preferably comprise a post-crosslinked outer region. Usually, water-absorbing polymer structures of this type have a core-shell morphology. Preferably, the inorganic fine particles are provided on or in or on and in the outer region.

Polymer structures preferred according to the invention are fibers, foams or particles, whereby fibers and particles are preferred and particles are particularly preferred.

Polymer fibers preferred according to the invention are dimensioned such that they can be incorporated in or as yarns for textiles and also directly in textiles. It is preferred according to the invention that the polymer fibers have a length in a range from 1 to 500, preferably 2 to 500 and particularly preferably 5 to 100 mm and a diameter in a range from 1 to 200, preferably 3 to 100 and particularly preferably 5 to 60 denier.

Polymer particles preferred according to the invention are so dimensioned that they have an average particle size according to ERT 420.2-02 in a range from 10 to 3000 µm, preferably 20 to 2000 µm and particularly preferably 150 to 850 µm. It is further preferred that the amount of particles with a particle size in a range from 300 to 600 µm is at least 50 wt. %, particularly preferably at least 75 wt. %.

A further contribution to the solution of the above-described objects is provided by a composite comprising the water-absorbing polymer structures according to the invention or water-absorbing polymer structures which are obtainable by radical polymerization of the acrylic acid obtainable by the above-described synthesis process in the presence of crosslinkers, and a substrate. It is preferred that the polymer structures according to the invention and the substrate are firmly bound with each other. As substrates are preferred sheets made from polymers, such as, for example, from polyethylene, polypropylene or polyamide, metals, non-wovens, fluff, tissues, woven materials, natural or synthetic fibers or other foams. It is further preferred according to the invention that the polymer structures are comprised in the composite in an amount of at least 50 wt. %, preferably at least 70 wt. % and yet more preferably at least 90 wt. %, based on the total weight of polymer structure and substrate.

In a particularly preferred embodiment of the composite according to the invention, this is a sheet-like composite, as described in WO-A-02/056812 as "absorbent material". The disclosure of WO-A-02/056812, in particular with respect to the exact construction of the composite, the mass per unit area of its components as well as its thickness is herewith introduced as reference and forms a part of the disclosure of the present invention.

A further contribution to the solution of the above-mentioned objects is provided by a process for production of a composite, wherein the water-absorbing polymer structures according to the invention or the water-absorbing polymers which are obtainable by radical polymerization of the acrylic acid obtainable by the above-described synthesis process in the presence of crosslinkers, and a substrate, and optionally an additive are brought into contact with each other. As substrate, preferably those substrates are used which have already been mentioned in connection with the composite according to the invention.

The contribution to the solution to the above-mentioned objects is also provided by a composite obtainable according to the above-described process.

A further contribution to the solution of the above-mentioned objects is made by chemical products comprising the water-absorbing polymer structures according to the invention or a composite according to the invention. Preferred chemical products are, in particular, foams, molded articles, fibers, sheets, films, cables, sealing materials, liquid absorbing hygiene articles, in particular diapers and feminine hygiene products, carriers for plant or fungus growth regulating agents or plant protection agents, additives for construction materials, packaging materials or soil additives. Preferred chemical products are hygiene articles, comprising a top-sheet, a bottom-sheet and a between-sheet arranged between the top-sheet and the bottom-sheet, which comprises water-absorbing polymer structures according to the invention.

In addition, the invention relates to a process for production of acrolein, which is characterized by the herein described process for dehydration of glycerine to a dehydration product comprising acrolein and the herein-described preferred embodiment of this dehydration.

Furthermore, the invention relates to fibers, sheets, adhesives, cosmetics, molding materials, textile and leather additives, flocculants, coatings or varnishes based on acrylic acid which is obtainable according to a process according to the invention or derivatives or salts thereof. As derivatives of acrylic acid are considered in particular its esters, preferably its alkyl esters and yet more preferably its $C_1$ to $C_{10}$, yet more preferably $C_2$ to $C_5$ and further preferably $C_3$ to $C_4$ alkyl esters. As salts, the alkaline or alkaline earth as well as the ammonium salts of acrylic acid should be mentioned.

Furthermore, the invention relates to the use of an acrylic acid, which has been obtained by a process according to the invention, or of derivatives or salts thereof, in fibers, sheets, adhesives, cosmetics, molding materials, textile and leather additives, flocculants, coatings or varnishes.

The invention is now more closely illustrated by means of non-limiting figures and examples.

FIG. 7 show in a) to c) embodiments of inserts according to the invention in cross-section.

Figure 1:
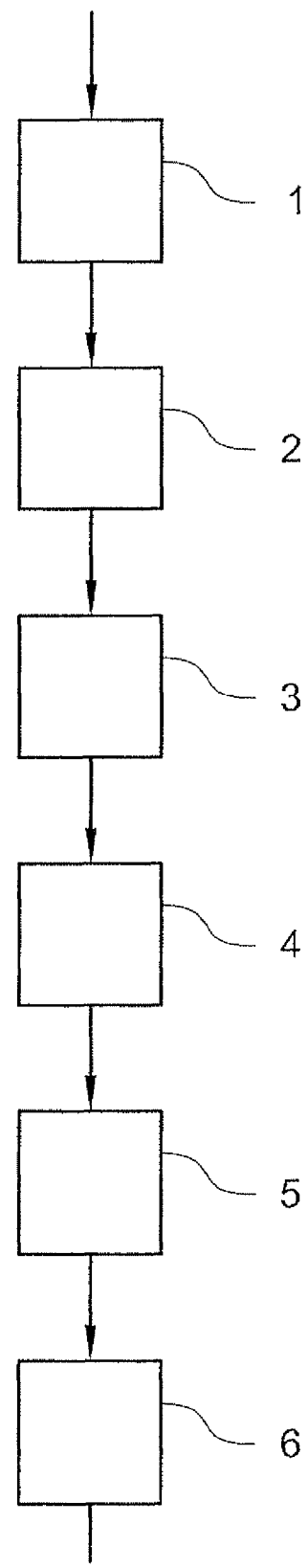
FIG. 1 shows schematically a schematic operation of the individual stages and steps of the process according to the invention and of the device according to the invention.

In FIG. 1, first the oils or fats are introduced into a saponifier 1, where an alkali saponification with soda or alkali alcoholates occurs. The glycerine obtained in the saponifier is then conducted to a dehydration unit with a dehydration reactor 2 (in order to obtain acrolein from the glycerine). The thus-obtained acrolein is then in a next step conducted to a gas phase reactor 3, in which it is converted by gas phase oxidation reaction to acrylic acid. After the gas phase reactor 3 follows a quench unit 4, in which the acrylic acid-comprising gas from the gas phase reactor 3 is brought into the liquid phase by bringing into contact with a quench agent. The liquid mixture of a quench agent and acrylic acid is conducted to a work-up unit 5 following the quench unit 4. There, the acrylic acid is purified either by crystallization or distillation or a combination of these two steps or by extraction or a combination of extraction and crystallization or a combination of extraction and distillation or a combination of extraction distillation and distillation to pure acrylic acid (at least 99.98% acrylic acid), which is present either as pure acrylic acid itself or in an aqueous phase. The thus-obtained acrylic acid is then conducted to a polymerization unit 6. The polymer obtained in the polymerization unit 6 can be manufactured according to the subsequent use. After the polymerization unit 6, a further processing unit, for example a diaper machine or machine for production of bandaging and wound material can follow.

Figure 2:
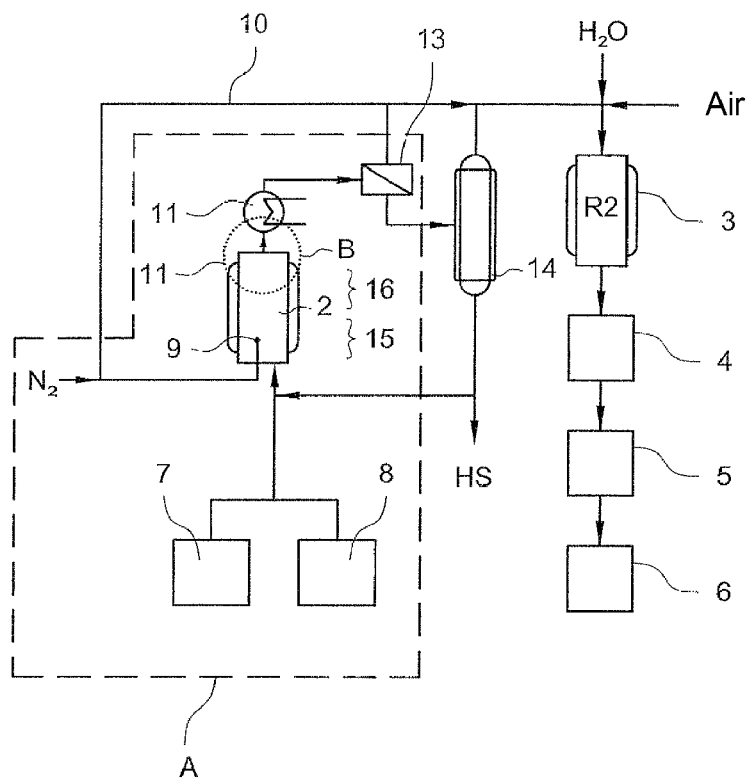
FIG. 2 shows schematically a dehydration unit followed by a gas phase oxidation unit.
Figure 3:
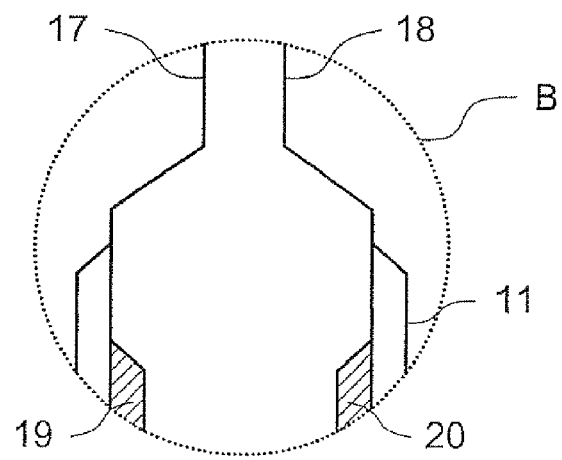
FIG. 3 shows a section B of the dehydration reactor as longitudinal section.

In FIG. 2, out of a reagent reservoir 7, which can be connected either via a line with the saponifier 1, or indirectly with this saponifier 1 by means of transport means such as a tank vehicle, a mostly aqueous glycerine solution is fed into a dehydration reactor 2 in the lower region of the dehydration reactor 2. For the case that liquid catalyst is used, a liquid catalyst container 8 is provided, which is connected via a line likewise with the reactor 2, whereby it is preferred that the glycerine and/or the aqueous glycerine phase and the liquid catalyst are conducted together before the feeding into the reactor 2. This can occur, for example, by prior connecting of the two lines of the reagent container 7 and the liquid catalyst container 8 via a static mixer or another mixing device (not shown) appearing suitable to the skilled person. Furthermore, the dehydration reactor comprises in its lower region a gas bubble generator 9 formed as a metal fritte, which is supplied from a gas conduit 10 with gas suitable for generation of bubbles. The gas conduit 10 can be linked not only with the dehydration reactor 2 but also with the gas phase oxidation reactor 3. The dehydration reactor 2 can furthermore be heated by means of a heating device 11. By means of the heating device 11, in addition to the gas supplied, a corresponding pressure relationship is generated in the dehydration reactor 2, so that, on the one hand, a liquid, and on the other hand, a gaseous face forms in the dehydration reactor 2. Attention should be paid that the gas bubble generator 9 is covered by the liquid phase located in the lower region 15. At the upper region of the dehydration reactor which is designed as pressure container, a heat exchanger 12 is connected, in which the gas coming from the upper region 16 of the dehydration reactor 2 is reduced in pressure and cooled. At the heat exchanger 12 is connected a separation container 13, in which the gaseous and liquid components which leave the heat exchanger 12 are separated. At the region of the separation container 13 which takes up the liquids is connected a distillation column 14. There, the acrolein as gaseous component via the head, and the high-boilers, which also mostly comprise glycerine, in the bottom, are separated. The high-boilers and the glycerine are piped away from the bottom of the distillation column and the glycerine further conducted to the dehydration reactor 2 and the high-boilers marked as "HS" conducted to a further use. The gaseous acrolein leaving the distillation column 14 overhead is conducted, with amounts of air and water necessary for the gas phase oxidation, to the gas phase oxidation reactor 3. The acrylic acid-comprising gas-mixture forming in the gas phase oxidation is then conducted to the quench unit 4, there, correspondingly prepared, so that, in the work-up unit 5, acrylic acid is obtained in desired purity. If a polymerization should occur, this can be conducted to the polymerization unit 6.

Section B of the upper region 16 of the dehydration reactor 2, a conically formed narrowing 17 is provided, which ends with the outlet 18 leading in the direction of the gas phase oxidation reactor. Furthermore, an embodiment of the device according to the invention for the operation with solid catalyst 19 is depicted. This is held by a solid state catalyst receiver 20, in particular if it is in the form of pellets.

Figure 4:
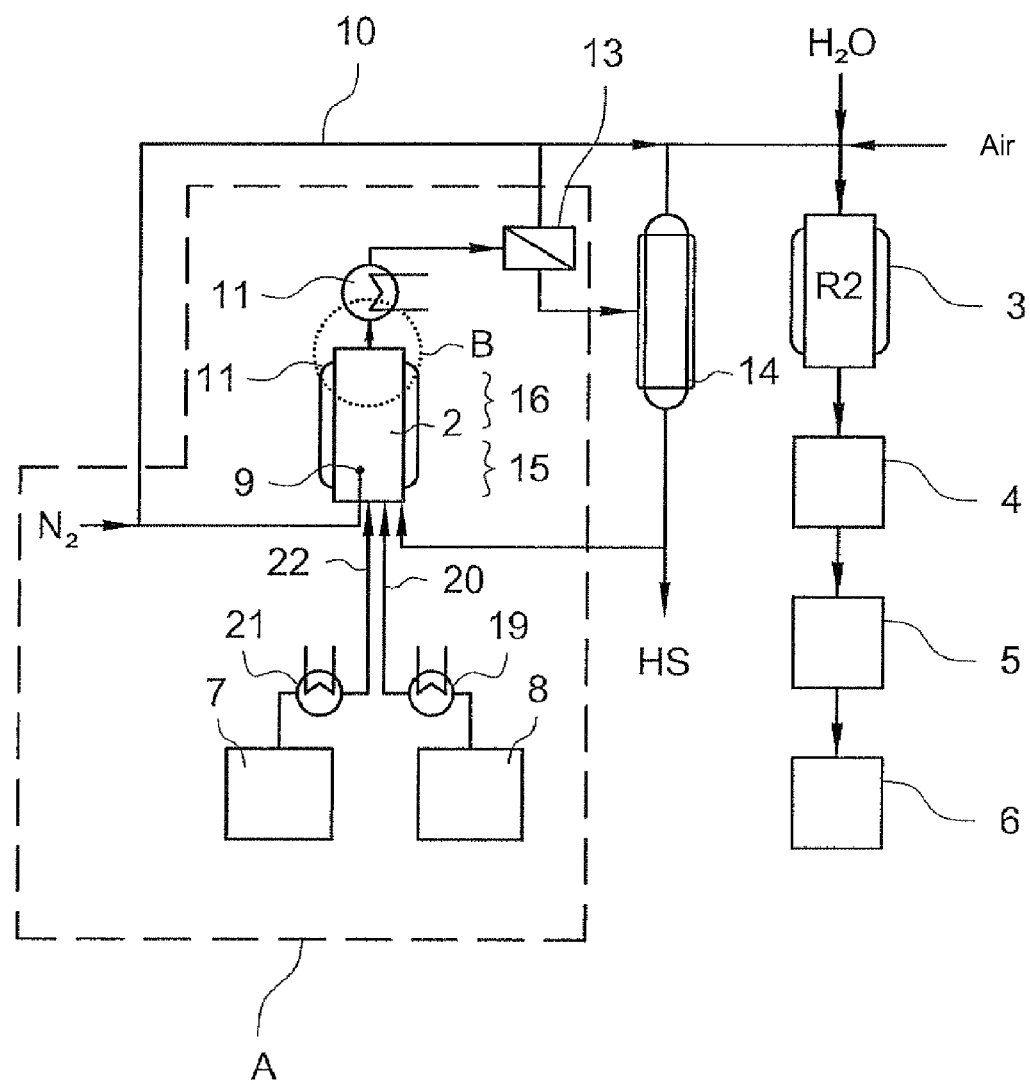
FIG. 4 shows schematically a further dehydration unit followed by a gas phase oxidation unit.

In FIG. 4, a further embodiment of the dehydration unit illustrated in FIG. 2, followed by a gas phase oxidation unit, with the following differences, is shown. Except for the following differences, the details concerning FIG. 2 also apply here. Different to FIG. 2, the liquid catalyst from the liquid catalyst container 8 is fed, separately from the reagent, into dehydration reactor 2, via a catalyst heat exchanger 19, which is provided in a catalyst line 20, and in which the catalyst can be pre-warmed. The reagent is likewise fed into the dehydration reactor 2 separately from the catalyst, via a reagent heat exchanger 21, in a warmable way by means of reagent line 22. By these measures, a combination of reagent and liquid catalyst first occurs in the dehydration reactor.

Figure 5:
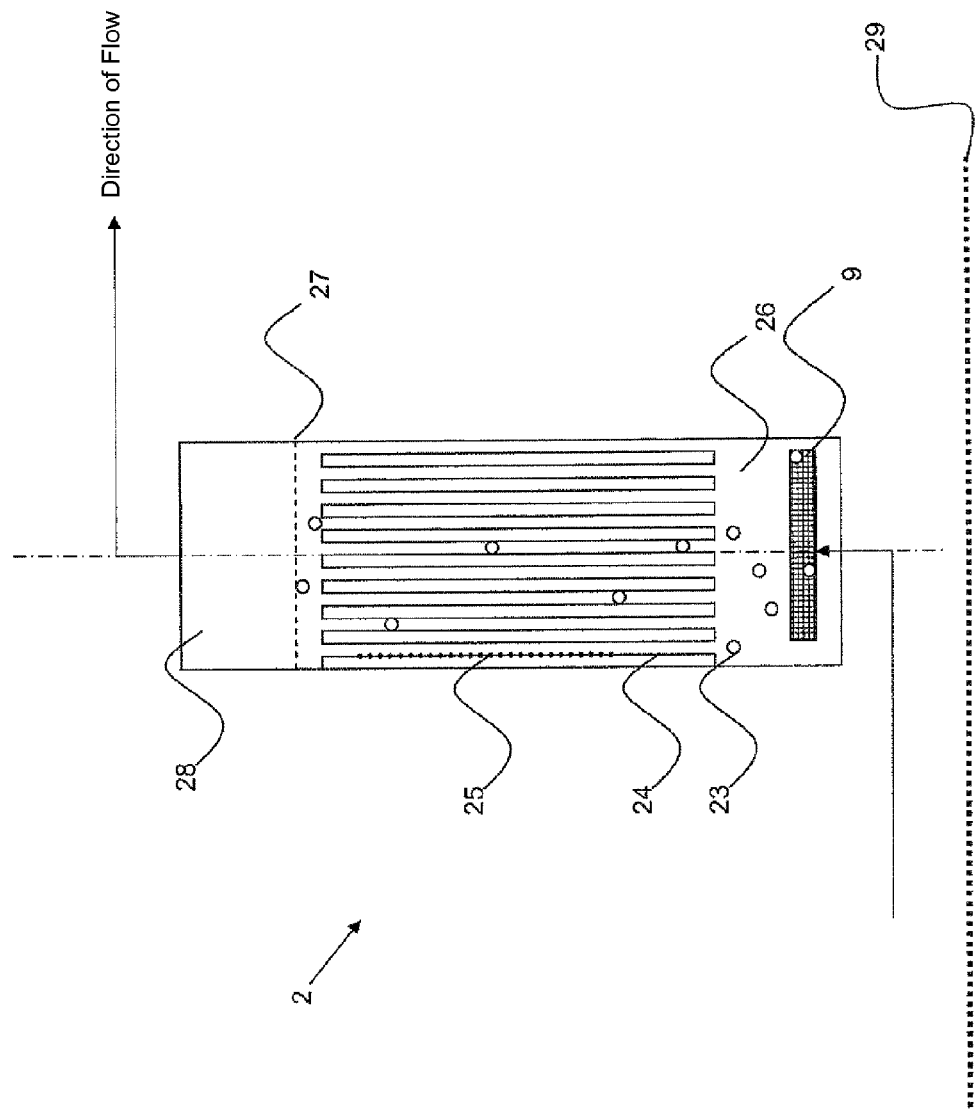
FIG. 5 shows schematically a longitudinal section through a dehydration reactor according to the invention.

FIG. 5 describes a longitudinal section of a dehydration reactor 2, in which gas bubbles are generated by a gas bubble generator 9. Here, the gas bubble generator 9 should be formed so that the gas bubbles 23 flow as uniformly as possible towards the insert 24 which can be flowed through which is provided above the gas bubble generator 9. The gas bubbles 23 generated by the gas bubble generator 9 migrate through the insert 24 which can be flowed through and which is here designed as multitube, and which can be slowed by adhesion by means of slowing area 25, which is here depicted as roughened surfaces of the pipe inner sides of the multitube pipe. In addition, the cross-section of the pipes determines the average size of the gas bubbles migrating through the insert which can be flowed through, which only leave the insert 24 which be flowed through in the liquid phase 26 below the phase border 27 before entry into the gas phase 28.

The dehydration reactor is arranged, with the upright pipes of the multitube as insert 24 which can be flowed through, on a floor 29.

Figures 6A, 6B:
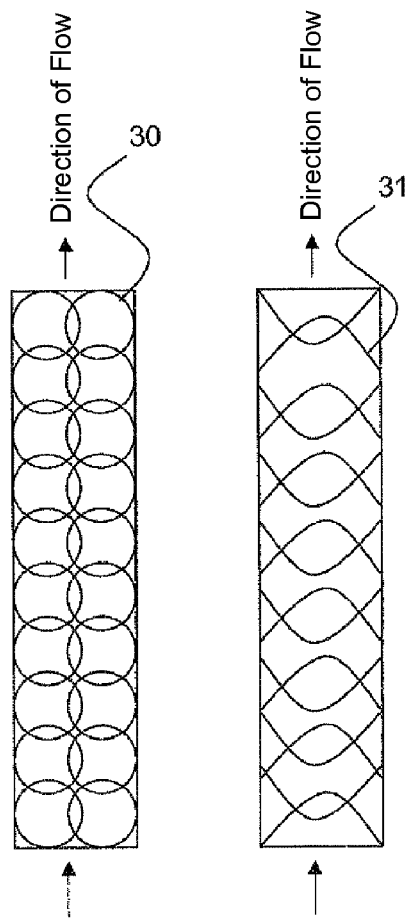
FIG. 6 show in a) and b) embodiments of inserts which can be flowed through according to the invention in longitudinal section.

FIGS. 6a and 6b show two different embodiments of inserts which can be flowed through. In FIG. 6a, rings 30 connected with each other are provided as inserts which can be flowed through. In FIG. 6b, loops 31 interlaced with each other are provided as inserts which can be flowed through.

FIGS. 7a, b and c show respectively different inserts which can be flowed through in a section through a pipe dehydration reactor. In FIG. 7a, star-shaped arranged deflectors are provided as star inserts 32, whereby the deflectors extend from one side to the other side of the reactor wall. Furthermore, a slowing region 25 is depicted by way of example as surface roughening on one of these deflectors. FIG. 7b shows a comparable arrangement to 7a of deflectors which are provided as cross inserts 33. FIG. 7c shows a construction comparable with FIGS. 7a and 7b, whereby instead of the deflectors, a multitube insert 34 is provided. The individual pipes of the multitube show a flow cross-section 36 in a section through the space 37 which is flowed through of one of the pipes of the multitube. In the case of FIG. 7b, the determination of the flow cross-section is shown by way of example. A cross-section circle 38, shown with a dashed line, is placed into the area of the inserts arising from the reactor cross-section, the circle lying tangentially at least three places. The flow cross-section 36 which is formed by the inserts for allowing through the gas bubbles arises from two times the radius of this circle.

EXAMPLES

Example 1

Liquid Phase Dehydration

Example 1a

In a device according to section A (framed with a dashed line) of FIG. 2, an aqueous (5%) glycerine solution, which has previously been brought to a pH-value of 2.3 with phosphoric acid, is fed in for liquid phase dehydration. The solution is heated in the reactor to 283° C. at 58 bar and an average residence time of 9 minutes. By means of a metal fritte, nitrogen is bubbled into the reactor. The nitrogen gas charge relative to the reactor volume and hours was 41 Nml. The glycerine conversion was 61% and the selectivity for acrolein was 85.6%.

Example 1b

In a device according to section A of FIG. 2, an aqueous (5%) glycerine solution, which had been previously brought to a pH-value of 2.3 with phosphoric acid, was fed in for liquid phase dehydration. The solution was heated in the reactor to 285° C. at 61 bar and an average residence time of 9 minutes. By means of a metal fritte, nitrogen was bubbled into the reactor. The nitrogen gas charge based on the reactor volume and hours was 41 Nml. The glycerine conversion was 72.1% and the selectivity for acrolein was 74.8%.

Example 1c

Example 1b was carried out on the one hand over 310 hours without nitrogen flushing and, on the other hand, over 460 hours with nitrogen flushing. Upon cleaning the dehydration reactor, in the operation without nitrogen, 21 g of solid soot-like, polymeric residues were obtained, and in the operation with nitrogen, 8 g of these residues.

Example 1d

In a device according to section A (framed with a dashed line) of FIG. 4, an aqueous (5%) glycerine solution and phosphoric acid, which were each heated respectively by means of a separated heat exchanger (19, 21) with a thermal-oil with a temperature of 283° C. are fed in for liquid phase dehydration, whereby the amount of phosphoric acid was selected so that the mixture of phosphoric acid and glycerine has a pH-value of 2.3. The solution was heated in the reactor to 283° C. at 58 bar and an average residence time of 9 minutes. By means of a metal fritte, nitrogen was bubbled into the reactor. The nitrogen gas charge, based on reactor volume and hours, was 41 Nml. The glycerine conversion was 61% and the selectivity for acrolein was 85%. The heat exchangers were fully functional after 400 h, no blockages were present.

Example 1e

Example 1d was repeated, whereby, different thereto, phosphoric acid and glycerine solution were conducted as a mixture through a heat exchanger and heated there. The glycerine conversion was 63.5% and the selectivity for acrolein was 61.3%.

Example 2

Gas Phase Oxidation

Following the acrolein synthesis, a gas phase oxidation of the acrolein produced in examples 1a to 1e occurred in a commercial gas phase oxidation reactor, followed by absorption in water in a quench unit. For the gas phase oxidation, a vapor-form 180 to 220° C. hot gas phase with a composition of 15 wt. % acrolein, 82 wt. % water vapor and a remainder of other light-boiling components analogous to WO 03/051809 A1 together with 1.5 kg/h pre-heated air were conducted into a gas phase oxidation reactor which is filled with 1.8 l commercial V—Mo-multioxide catalyst.

The acrylic acid-water mixtures obtained in example 1a and 1b were combined in a glass separating funnel cooled to 0° C. with 0.5 parts of the volume of toluene. The mixture was shaken vigorously and allowed to stand for 60 minutes, in order to enable a phase separation. The two phases thus arising were separated. The toluene-comprising phase was subjected to an azeotropic distillation and the thus-obtained acrylic acid was distilled again before its use for polymerization.

Example 3

Polymerization

Example 3.0

Production of a Non-Surface Post-Crosslinked Polymer Structure—Powder A

A monomer solution consisting of 280 g of the above-produced and freshly distilled acrylic acid, which was neutralized to 70 mol % with sodium hydroxide, 466.8 g water, 1.4 g poly-ethyleneglycol-300-diacrylate and 1.68 g allyloxypolyethyleneglycol acrylic acid ester was purged with nitrogen to remove the dissolved oxygen and cooled to the start temperature of 4° C. After reaching the start temperature, the initiator solution (0.1 g 2,2'-azobis-2-amidinpropan-dihydrochloride in 10 g $H_2O$, 0.3 g sodium peroxydisulfate in 10 g $H_2O$, 0.07 g 30% hydrogen peroxide solution in 1 g $H_2O$ and 0.015 g ascorbic acid in 2 g $H_2O$) added. After the end temperature of about 100° C. was reached, the gel formed was comminuted and dried and 150° C. for 90 minutes. The dried polymer was coarsely chopped, milled and sieved to a powder with a particle size of 150 to 850 μm. The powder A has a retention according to ERT 441.2-02 of 28.8 g/g.

Example 3.1

Preparation of a Surface Post-Crosslinked Polymer Structure in the Presence of a Silica Sol 50 g of powder A was intimately mixed by means of a Krups-Kitchen-Mixer with a solution of 0.5 g ethylene carbonate, 0.42 g silica sol (product Levasil® 200 from Bayer AG, solid portion about 30 wt. %) and 1.08 g water with stirring, and then heated for 30 minutes in an oven set to 180° C. The properties of the thus-obtained powder are given in the following table.

Example 3.2

Preparation of a Surface Post-Crosslinked Polymer Structure in the Presence of a Silica Sol 50 g of powder A was intimately mixed by means of a Krups-Kitchen-Mixer with a solution of 0.5 g ethylene carbonate, 0.84 g silica sol (product Levasil® 200 from Bayer AG, solid portion about 30 wt. %) and 0.66 g water with stirring, and then heated for 30 minutes in an oven set to 180° C. The properties of the thus-obtained powder are given in the following table.

TABLE

| Example | SFC [$10^{-7} \cdot cm^3 \cdot s \cdot g^{-1}$] | AAP (0.7 psi) [g/g] | CRC [g/g] |
|---|---|---|---|
| 3.1 | 140 | 23.5 | 27 |
| 3.2 | 150 | 23.5 | 27.2 |

Example 3.3

Production of a Biodegradable Polymer

The polymer obtained in example 3.1 was mixed under dry conditions with a water-soluble wheat starch (the product Foralys® 380 from the company Roquette, Lestrem, France) in weight ratio polymer: starches of 4:1 and then further homogenized for 45 minutes in a roll mixer type BTR 10 of the company Fröbel GmbH, Germany.

Example 4

Liquid Phase Dehydration with Inserts which can be Flowed Through

Example 4a

In a device designed with a flow-pipe as dehydration reactor according to section A (framed in dashed region) of FIG. 2, an aqueous (5%) glycerine solution and an aqueous phosphoric acid solution (50%) are introduced, whereby each solution has previously been heated by means of a heat exchanger to 250° C. at 56 bar. The material streams are selected so that in the dehydration reactor a glycerine concentration of 7 wt. %, based on the total reaction mixture is achieved. The concentration of the phosphoric acid was adjusted in the reaction mixture to a pH value of 2. The reactor was heated by means of heat carrier oil via an outer wall heating to reactor inner temperature of 280° C. and maintained at this temperature. The reaction mixture after exit from the reactor was cooled to room temperature and pressure reduced to normal pressure so that samples could be analyzed by means of gas chromatography. The reactor was charged with a reaction mixture of 6 l per hour, the reaction volume was 2 l.

Example 4b

The reactor from example 4a was operated without additional inserts. With a conversion of 8%, the selectivity for acrolein was 79%.

Example 4c

In the reactor from example 4a, plates were introduced into the flow pipe, so that the flow channel formed by the flow pipe was divided into four segments (compare FIG. 7b). The conversion could be increased to 24% with a selectivity for acrolein of 79%.

Example 4d

Into the flow pipe of the reactor from example 4, a pipe bundle (multitube) with 16 pipes was provided. The turnover of the thus-formed reactor was 60% with the selectivity for acrolein of 79%.

Test Methods

Determination of the SFC-Value

The determination of the permeability in swollen state (Saline Fluid Conductivity=SFC) occurs according to a method described in WO-A-95/22356. About 0.9 g superabsorber material (with particles, the whole particle fraction) are weighed into a cylinder with a sieve floor and carefully distributed on the sieve surface. The superabsorber material was allowed to swell for one hour in JAYCO synthetic urine against a pressure of 0.7 psi. After measuring the swell height of the superabsorber, 0.118 M NaCl solution from a graduated reservoir is allowed to flow through the swollen gel sheet at constant hydrostatic pressure. The swollen gel sheet is covered with a special sieve cylinder during the measurement, which ensures a uniform distribution of the 0.118 M NaCl solution above the gel and constant conditions (measurement temperature 20-25° C.) during the measurement in respect of the gel bed property. The pressure acting on the swollen superabsorber is still 0.7 psi. Using a computer and a balance, the amount of liquid which passes through the gel sheet as a function of time is determined in intervals of 20 seconds over a time period of 10 minutes. The flow rate in g/s through the swollen gel sheet is determined by means of regression analysis with extrapolation of the gradient and determination of the central point at the time point t=0 of the flow amount within the minutes 2-10. The SFC value (K) is given in $cm^3 \cdot s \cdot g^{-1}$ and calculated as follows:

$$K = \frac{F_s(t=0) \cdot L_0}{r \cdot A \cdot \Delta P_l} = \frac{F_s(t=0) \cdot L_o}{139506}$$

whereby:
$F_s(t=0)$ is the flow rate in g/s,
$L_0$ is the thickness of the gel sheet in cm,
R is the density of the NaCl solution (1.003 g/cm³),
A is the surface of the upper side of the gel layer in the measuring cylinder (28.27 cm²),
ΔP is the hydrostatic pressure which acts upon the gel sheet (4920 dyne/cm²), and
K is the SFC value [$cm^3 s g^{-1}$].

Determination of the Retention

The retention described as CRC is determined according ERT 441.2-02, whereby "ERT" stands for "EDANA recommended Test" and "EDANA" for European Disposable and Nonwovens Association".

Determination of the Absorption Against Pressure

The absorption against a pressure of 0.7 psi described as AAP is determined according to ERT 442.2-02.

Determination of the Biodegradability

The determination of the biodegradability occurs according to the Sturm-test according to appendix V to guideline 67/548/EEC.

LIST OF REFERENCE NUMERALS 1 saponifier
2 dehydration reactor
3 gas phase reaction reactor
4 quench unit
5 work-up unit
6 polymerization
7 reagent container
8 liquid catalyst container
9 gas bubble generator
10 gas conduit
11 heating device
12 heat exchanger
13 separating container
14 distillation column
15 lower region
16 upper region
17 narrowing
18 outlet
19 catalyst heat exchanger
20 catalyst lead
21 reagent heat exchanger
22 reagent line
23 gas bubbles
24 insert which can be flowed through
25 slowing region
26 liquid phase
27 phase border
28 gas phase
29 floor
30 rings
31 loops
32 star inserts
33 cross inserts
34 multitube inserts
35 reactor wall
36 flow cross section
37 section through space flowed through
38 cross-section circle

What is claimed is:

1. A process for preparation of a polymer by polymerization of acrylic acid, comprising the following steps:
   A heating an aqueous glycerine solution before entry into a dehydration reactor to a temperature of from about 250° C. to 310° C. to form glycerine;
   B transporting the glycerine of step A to the dehydration reactor;
   C dehydrating the glycerine of step B to an acrolein-comprising dehydration product wherein the dehydrating occurs along a path wherein the glycerine concentration decreases, wherein along this path a pressure change occurs, and different flow rates exist;
   D gas phase oxidating of the acrolein-comprising dehydration product to obtain an acrylic acid-comprising monomer gas;
   E bringing into contact of the monomer gas with a quench agent to obtain an acrylic acid-comprising quench phase;
   F working-up the quench phase to obtain an acrylic acid-comprising monomer phase; and
   G polymerizing the acrylic acid-comprising monomer phase;
   wherein during the dehydration a liquid phase a1 and a gas phase a2 is present, wherein in the liquid phase a1, a plurality of gas bubbles is generated wherein the dehydration occurs at least partially in the liquid phase.

2. The process according to claim 1, wherein the polymer is a water-absorbing polymer structure.

3. The process according to claim 1 wherein the acrylic acid is present to at least about 20 mol %, based on the monomer, as a salt.

4. The process according to claim 1 wherein at least a part of the plurality of gas bubbles within the liquid phase a1 is conducted.

5. The process according to claim 1 wherein at least a part of the plurality of gas bubbles within the liquid phase a1 is divided.

6. The process according to claim 1 wherein the glycerine is obtained by saponification of fats.

7. The process according to claim 1 wherein the glycerine is produced in the generation of liquid carburants from natural raw materials.

8. The process according to claim 1 wherein the dehydration occurs at a temperature in a range from 100° C. to 400° C.

9. The process according to claim 1 wherein the dehydration occurs at a pressure in a range from 2 to 200 bar.

10. The process according to claim 1 wherein the dehydration occurs with an average reactor residence time in a range from 1 to 30 minutes.

11. The process according to claim 1 wherein the acrolein arising from the dehydration is transferred by the plurality of gas bubble out of the liquid phase a1 into the gas phase a2.

12. The process according to claim 1 wherein the glycerine is warmed to from 270° C. to 290° C.

* * * * *